US009636632B2

(12) United States Patent
Merkel et al.

(10) Patent No.: US 9,636,632 B2
(45) Date of Patent: May 2, 2017

(54) GAS SEPARATION MEMBRANES BASED ON FLUORINATED AND PERFLUORINATED POLYMERS

(71) Applicants: Membrane Technology and Research, Inc., Newark, CA (US); New York University, New York, NY (US)

(72) Inventors: Timothy C Merkel, San Jose, CA (US); Hao Zhang, Fremont, CA (US); Zhenjie He, Fremont, CA (US); Yoshiyuki Okamoto, Brooklyn, NY (US)

(73) Assignees: Membrane Technology and Research, Inc, Newark, CA (US); New York University, New York, NY (US)

( * ) Notice: Subject to any disclaimer, the term of this patent is extended or adjusted under 35 U.S.C. 154(b) by 0 days.

(21) Appl. No.: 15/141,303

(22) Filed: Apr. 28, 2016

(65) Prior Publication Data
US 2016/0236141 A1 Aug. 18, 2016

Related U.S. Application Data

(63) Continuation-in-part of application No. 14/921,382, filed on Oct. 23, 2015, which is a continuation-in-part of application No. 14/330,714, filed on Jul. 14, 2014, which is a continuation of application No. 14/184,308, filed on Feb. 19, 2014, now Pat. No. 8,828,121.

(60) Provisional application No. 62/154,408, filed on Apr. 29, 2015.

(51) Int. Cl.
*B01D 53/22* (2006.01)
*B01D 71/32* (2006.01)
*B01D 71/38* (2006.01)

(52) U.S. Cl.
CPC .......... *B01D 53/228* (2013.01); *B01D 71/32* (2013.01); *B01D 71/38* (2013.01); *B01D 2256/245* (2013.01); *B01D 2257/102* (2013.01); *B01D 2257/108* (2013.01); *B01D 2257/11* (2013.01); *B01D 2257/504* (2013.01); *Y02C 10/10* (2013.01)

(58) Field of Classification Search
CPC ...... B01D 53/22; B01D 53/228; B01D 71/06; B01D 71/32; B01D 2256/245; B01D 2257/102; B01D 2257/108; B01D 2257/11; B01D 2257/504
See application file for complete search history.

(56) References Cited

U.S. PATENT DOCUMENTS

| 3,133,132 A | 5/1964 | Loeb et al. |
| 3,307,330 A * | 3/1967 | Niedzielski ............ B01D 53/22 95/45 |
| 3,308,107 A | 3/1967 | Selman et al. |
| 4,230,463 A | 10/1980 | Henis et al. |
| 4,243,701 A | 1/1981 | Riley et al. |
| 4,863,761 A | 9/1989 | Puri |
| 5,051,114 A * | 9/1991 | Nemser ................ B01D 53/228 95/47 |
| 5,141,642 A | 8/1992 | Kusuki et al. |
| 5,156,888 A | 10/1992 | Haubs et al. |
| 5,242,636 A | 9/1993 | Sluma et al. |
| 5,265,734 A | 11/1993 | Linder et al. |
| 5,318,417 A | 6/1994 | Kopp et al. |
| 5,408,020 A | 4/1995 | Hung et al. |
| 6,361,582 B1 | 3/2002 | Pinnau et al. |
| 6,361,583 B1 | 3/2002 | Pinnau et al. |
| 6,406,517 B1 * | 6/2002 | Avery .................. B01D 53/228 55/524 |
| 6,544,316 B2 | 4/2003 | Baker et al. |
| 6,572,679 B2 | 6/2003 | Baker et al. |
| 6,572,680 B2 | 6/2003 | Baker et al. |
| 6,579,341 B2 | 6/2003 | Baker et al. |
| 6,592,650 B2 | 7/2003 | Pinnau et al. |
| 7,078,470 B2 | 7/2006 | Funaki et al. |
| 7,582,714 B2 | 9/2009 | Okamoto et al. |
| 7,635,780 B2 | 12/2009 | Okamoto et al. |
| 7,690,514 B2 | 4/2010 | McKeown et al. |
| 7,754,901 B2 | 7/2010 | Okamoto et al. |
| 8,056,732 B2 | 11/2011 | McKeown et al. |
| 8,168,808 B2 | 5/2012 | Okamoto et al. |
| 8,575,414 B2 | 11/2013 | Liu et al. |

(Continued)

FOREIGN PATENT DOCUMENTS

| JP | 4032738 B2 | 1/2008 | |
| WO | WO 2010/080753 A1 * | 7/2010 | ............. B01D 39/16 |
| WO | WO2010080753 A1 | 7/2010 | |

OTHER PUBLICATIONS

Yang, et al, "Novel Amorphous Perfluorocopolymeric System; Copolymers of Perfluoro-2-methylene-1,3-dioxolane Derivatives," Journal of Polymer Science, vol. 44, pp. 1613-1618 (2006).

Liu, et al., Synthesis and Radical Polymerization of Perfluoro-2-methylene-1,3-dioxolanes, Macromolecules, vol. 38, pp. 9466-9478 (2005).

Koike, et al, Synthesis and Characterization of Copolymers of Perfluoro(2-methylene-4,5-dimethyl-1,3-dioxolane) and Perfluoro(2-methylene-1,3-dioxolane), Journal of Fluorine Chemistry, vol. 156, pp. 198-202 (2013).

(Continued)

*Primary Examiner* — Jason M Greene
(74) *Attorney, Agent, or Firm* — Timothy A. Hott

(57) ABSTRACT

A process for separating components of a gas mixture using gas-separation copolymer membranes. These membranes use a selective layer made from copolymers of an amorphous perfluorinated dioxolane and a fluorovinyl monomer. The resulting membranes have superior selectivity performance for gas pairs of interest while maintaining fast gas permeance compared to membranes prepared using conventional perfluoropolymers such as Teflon® AF, Hlyflon® AD, and Cytop®.

15 Claims, No Drawings

(56) References Cited

U.S. PATENT DOCUMENTS

| | | | |
|---|---|---|---|
| 8,686,104 | B2 | 4/2014 | Du et al. |
| 8,828,121 | B1* | 9/2014 | He .................. B01D 71/32 |
| | | | 95/45 |
| 9,079,138 | B2 | 7/2015 | Nemser et al. |
| 2011/0266220 | A1 | 11/2011 | Campos et al. |
| 2012/0097612 | A1 | 4/2012 | Nemser et al. |
| 2012/0190091 | A1 | 7/2012 | Huang et al. |
| 2015/0025293 | A1* | 1/2015 | Feiring ............. B01D 53/228 |
| | | | 585/818 |
| 2015/0031537 | A1 | 1/2015 | Dorner-Rieping et al. |
| 2015/0231555 | A1 | 8/2015 | He et al. |
| 2016/0002413 | A1 | 1/2016 | Wlassics et al. |

OTHER PUBLICATIONS

Mikes, et al, Characterization and Properties of Semicrystalline and Amorphous Perfluoropolymer: Poly(perfluoro-2-methylene-1,3-dioxolane), Polym. Adv. Technol. vol. 22, pp. 1272-1277 (2011).

Paul and Chio, "Gas Permeation in a Dry Nafion Membrane," Industrial and Engineering Chemistry Research, Inc., vol. 27, pp. 2161-2164 (1988).

Okamoto, et al, "Synthesis and Properties of Amorphous Perfluorinated Polymers," Chemistry Today, vol. 27, pp. 46-48 (2009).

Nakagawa,T., "Industrial Applications of Membranes for Gas Separation in Japan," in Polymeric Gas Separation Membranes, Ed. D.R. Paul and Y.P. Yampol'skii, pp. 416-419. Boca Raton, CRC Press (1994).

Liu,et al., "Free-Radical Polymerization of Dioxolane and Dioxane Derivatives: Effect of Fluorine Substituents on the Ring Opening Polymerization", Journal of Polymer Science Part A: Polymer Chemistry, vol. 42, pp. 5180-5188 (2004).

Okamoto, et al. "New Perfluoro-Dioxolane-Based Membranes for Gas Separations", Journal of Membrane Science, vol. 471, pp. 412-419 (2014).

Ezhov, "Permeability of Fluorine and Some Other Fluorine-Containing Gases Through Nonporous Fluorine-Stable Copolymers,"Atomic Energy, vol. 110, No. 3, pp. 207-211 (2011).

Ezhov, "Investigation of Permeability of Fluorine and Certain Fluorinated Gases Through Nonporous Fluorine-Resistant Polymers," Petroleum Chemistry, vol. 45, No. 8 pp. 608-611 (2014).

Mikes, et al, "Synthesis and Characterization of Perfluoro-3-methylene-2,4-dioxabicyclo[3,3,0] octane: Homo- and Copolymerization with Fluorovinyl Monomers," Journal of Polymer Science: Part A: Polymer Chemistry, vol. 47 pp. 6571-6578 (2009).

Boschet, et al, "(Co)polymers of Chlorotrifluoroethylene: Synthesis, Properties, and Applications," Chem. Rev. vol. 114 No. 2, pp. 927-980, paragraph 3.2.13, (2013).

Okamoto, et al., "Amorphous Polymers," in Handbook of Fluoropolymer Science and Technology, First Edition, John WIley and Sons, (2014).

Teng, "Overview of the Development of the Fluoropolymer Industry," Appl. Sci., vol. 2, pp. 496-412 (2012).

Annex to form PCT/ISA/206, Communication Relating to the Results of the Partial International Search for PCT/US2016/029817, mailed Jul. 27, 2016.

* cited by examiner

GAS SEPARATION MEMBRANES BASED ON FLUORINATED AND PERFLUORINATED POLYMERS

CROSS-REFERENCE TO RELATED APPLICATIONS

This application is a non-provisional application and claims the benefit of U.S. Provisional Patent Application No. 62/154,408, filed on Apr. 29, 2015, and is a continuation-in-part of U.S. Ser. No. 14/921,382, filed on Oct. 23, 2015, which is a continuation-in-part of U.S. Ser. No. 14/330,714, filed on Jul. 14, 2014, which is a continuation of Ser. No. 14/184,308, filed on Feb. 19, 2014 and issued as U.S. Pat. No. 8,828,121 on Sep. 9, 2014, all of which are hereby incorporated by reference in their entireties.

STATEMENT OF GOVERNMENT SUPPORT

The invention was made with Government support under Grant No. IIP-1449053 awarded by the National Science Foundation. The Government has certain rights in this invention.

FIELD OF THE INVENTION

The invention relates to membrane-based gas separation processes. In particular, the invention relates to gas separation processes using copolymer membranes having a selective layer comprising a perfluorinated dioxolane monomer and a fluorovinyl monomer.

BACKGROUND OF THE INVENTION

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

The search for a membrane for use in gas separation applications that combines high selectivity with high flux continues. Current perfluoropolymer membranes, such as those made from Hyflon® AD (Solvay), Teflon® AF (Du Pont), Cytop® (Asahi Glass), and variants thereof, have excellent chemical resistance and stability. We reported earlier, in U.S. Pat. No. 6,361,583, membranes that are made from glassy polymers or copolymers, including Hyflon® AD, and are characterized by having repeating units of a fluorinated, cyclic structure. In general, the ring structures in these materials frustrate polymer chain packing yielding amorphous polymers with relatively high gas permeability. These developed membranes are also more resistant to plasticization by hydrocarbons than prior art membranes and are able to recover from accidental exposure to liquid hydrocarbons.

It is known that copolymerization of fluorinated cyclic monomers with tetrafluoroethylene (TFE) enhances the chemical resistance and physical rigidity of membranes. TFE is also known to improve processability and has the effect of lowering gas permeability and increasing size selectivity in Hyflon® AD and Teflon® AF. Therefore, combinations of TFE with other monomer units, in particular perfluorinated dioxoles, such as in Teflon® AF and Hyflon® AD, that result in overall amorphous, yet rigid, highly fluorinated, copolymers are useful for industrial membrane applications. However, a drawback to these membranes is that their selectivities are relatively low for a number of gas pairs of interest, including $H_2/CH_4$, $He/CH_4$, $CO_2/CH_4$, and $N_2/CH_4$.

Other than the commercially available perfluoropolymers, there is very limited gas transport data available for fully fluorinated polymers. Paul and Chio, "Gas permeation in a dry Nafion membrane," Industrial & Engineering Chemistry Research, 27, 2161-2164 (1988), examined gas transport in dry Nation® (an ionic copolymer of TFE and sulfonated perfluorovinyl ether) and found relatively high permeabilities and selectivities for several gas pairs ($He/CH_4$, $He/H_2$, and $N_2/CH_4$) compared to conventional hydrocarbon-based polymers considered for membrane applications. Nafion® and related ionic materials are used to make ion exchange membranes for electrochemical cells and the like. Because of their high cost and need for carefully controlled operating conditions, such as adjusting the relative humidity of the feed gas to prevent polymer swelling and loss of performance, these ionic membranes are not suitable for industrial gas separations.

U.S. Pat. No. 5,051,114, to DuPont, discloses the testing of poly-[perfluoro-2-methylene-4-methyl-1,3-dioxolane] for use in a membrane for gas separation. The results indicated that this material exhibited gas permeabilities 2.5 to 40 times lower as compared to dipolymer membranes of perfluoro-2,2-dimethyl-1,3-dioxole and TFE, but had higher selectivities. Also disclosed are copolymers of perfluoro-2,2-dimethyl-1,3-dioxole and either tetrafluoroethylene, perfluoromethyl vinyl ether, vinylidene fluoride, or chlorotrifluorethylene.

Recently, there have been reports of new non-ionic amorphous perfluoropolymers, U.S. Pat. Nos. 7,582,714; 7,635,780; 7,754,901; and 8,168,808, all to Yoshiyuki Okamoto, disclose compositions and processes for making dioxolane derivatives.

Yang et al., "Novel Amorphous Perfluorocopolymeric System: Copolymers of Perfluoro-2-methylene-1,3-dioxolane Derivatives," Journal of Polymer Science: Part A: Polymer Chemistry, Vol. 44, 1613-1618 (2006), and Okamoto et al., "Synthesis and properties of amorphous perfluorinated polymers," Chemistry Today, vol, 27, n. 4, pp. 46-48 (July-August 2009), disclose the copolymerization of two dioxolane derivatives, perfluorotetrahydro-2-methylene-furo[3,4,-d][1,3]dioxolane and perfluoro-2-methylene-4-methoxymethyl-1,3-dioxolane. The copolymers were found to be thermally stable, have low refractive indices, and high optical transparency from UV to near-infrared, making them ideal candidates for use in optical and electrical materials.

Liu et al., "Free-Radical Polymerization of Dioxolane and Dioxane Derivatives: Effect of Fluorine Substituents on the Ring Opening Polymerization," Journal of Polymer Science: Part A: Polymer Chemistry, Vol. 42, 5180-5188 (2004), discloses the synthesis of partially- and fully-fluorinated dioxolane and dioxane monomers that may be used in materials for optical fiber applications.

Mikes et al., "Synthesis and Characterization of Perfluoro-3-methylene-2,4,-dioxabicyclo [3.3,0]octane: Homo- and Copolymerization with Fluorovinyl Monomers," J Polym Sci Part A: Polym Chem, 47: 6571-6578 (2009), discloses copolymers of perfluoro-3-methylene-2,3-dioxabicyclo-[3,3,0]octane with chlorotrifluoroethylene (CTFE), perfluoropropyl vinyl ether, perfluoromethyl vinyl ether, and vinylidene fluoride for use in a variety of applications.

Boshet and Ameduri, "(Co)polymers of Chlorotrifluoroethylene: Synthesis, Properties, and Applications," Chem.

Rev, 2014, 114, 927-980, discloses copolymers of chlorotrifluoroethylene and perfluoro-3-methylene-2,3-dioxabicyclo-[3,3,0]octane for use in optical fiber applications.

Paul and Yampol'ski, "Polymeric Gas Separation Membranes," CRC Press, pp. 416-419 (1994), discloses polymer membranes investigated by Asahi Glass Co. that contain a copolymer of tetrafluoroethylene and perfluoro-2-methylene-4-methyl-1-3-dioxolane. However, no gas separation data is presented.

U.S. Pat. No. 9,079,138 to Nemser et al., discloses a method for making fluorinated polymeric membranes comprising, for example, a copolymer of perfluoro-2-methylene-4-methyl-1,3-dioxolane and a fluorovinyl monomer, which can be used for separating liquid components under nanofiltration type operating conditions. These membranes have a high transmembrane flux, which is unsuitable for gas separation.

Ezhov, "Investigation of Permeability of Fluorine and Certain Gases through Nonporous Fluorine-Resistant Polymers," Petroleum Chemistry, 2014, Vol. 54, No, 8, pp. 608-611, and "Permeability of Fluorine and Some Other Fluorine-Containing Gases Through Nonporous Fluorine-stable Copolymers," Atomic Energy, 2011, Vol. 110, No. 3, pp. 173-175, disclose the separation of certain fluorinated gases using thick films (30-100 μm) made of copolymers of vinylidene fluoride and perfluoro-2-methylene-4-methyl-1, 3-dioxolane and perfluoro-2-methylene-1,3-dioxolane.

U.S. PGPUB 2012/0190091 to Huang et al. discloses a method for dehydrating organic/water solutions using a membrane having a selective layer formed from highly fluorinated monomers, including copolymers of dioxolanes and fluorinated ethers and ethylene. However, no specific dioxolanes are disclosed.

To date, however, we are unaware of any published data reporting gas separation performances of membranes made by copolymerizing perfluorodioxolane monomers with the fluorovinyl monomers as described herein.

SUMMARY OF THE INVENTION

The present invention relates to a process for separating components of a gas mixture whereby the gas mixture is passed across an improved separation membrane having a selective layer formed from a copolymer comprising of at least one dioxolane monomer and a fluorovinyl monomer.

As discussed above, membranes previously developed for gas separation processes lack adequate selectivity for certain gas separation, such as treatment of natural gas. To address the performance issues of these membranes, in co-owned U.S. Pat. No, 8,828,121, we previously examined the properties of certain specific dioxolane copolymers incorporating at least two perfluorinated dioxolane monomers of differing crystallinity. In particular, we discovered that copolymers of perfluorodioxolane monomers listed in Table 1, below, could be used as the selective layer in composite membranes having improved gas separation properties.

TABLE 1

Perfluorodioxolane Monomers

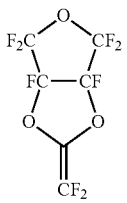

(Monomer A)

Perfluorotetrahydro-2-methylene-furo[3,4-d][1,3]dioxolane

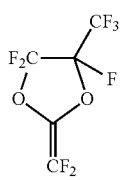

(Monomer B)

Perfluoro-2-methylene-4-methyl-1,3-dioxolane

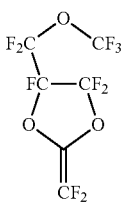

(Monomer C)

Perfluoro-2-methylene-4-methoxymethyl-1,3-dioxolane

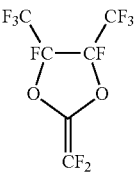

(Monomer D)

Perfluoro-2-methylene-4,5-dimethyl-1,3,-dioxolane

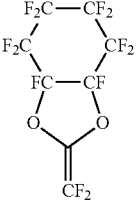

(Monomer E)

Perfluoro-3-methylene-2,4-dioxabicyclo[4,3,0]nonane

TABLE 1-continued

Perfluorodioxolane Monomers (Monomer F)

Perfluoro-3-methylene-2,4-dioxabicyclo[3,3,0] octane (Monomer G)

Perfluoro-2-methylene-4,5-dimethoxymethyl-1,3-dioxolane (Monomer H)

Perfluoro-2-methylene-1,3-dioxolane

Subsequent consideration and study of these materials has indicated that polymers incorporating even one perfluorodioxolane monomer may have special properties, including useful and stable gas separation properties. In sonic cases, the perfluorodioxolane monomer has certain properties such that when polymerized as a homopolymer, the homopolymer has no substantial crystallinity to it. That is, the homopolymer of the perfluorodioxolane is amorphous.

An important feature of the present invention is to balance the crystalline and amorphous phases of the copolymer material. If the copolymer is too crystalline or tightly packed, the membrane selective layer may have undesirably low permeability. Conversely, a looser, open or more flexible structure may result in a membrane with high fluxes, but poor selectivity. Therefore, the fluorovinyl monomer should be one that counterbalances the characteristics of the dioxolane monomer.

In certain aspects, the fluorovinyl monomer is selected from known monomers, such as those described in Mikes et al., "Synthesis and Characterization of Perfluoro-3-methylene-2,4-dioxabicyclo[3,3,0]octane: Homo-and Copolymerization with Fluorovinyl Monomers," J Polym Sci Part A: Polym Chem, 47: 6571-6578 (2009) or Teng, "Overview of the Development of the Fluoropolymer Industry," Appl. Sci, 2012, 2, 496-512, each incorporated herein by reference. These fluorovinyl monomers include, but are not limited to trifluoroethylene, tetrafluoroethylene (TFE), chlorotrifluoroethylene (CTFE), perfluoro methyl vinyl ether (PFMVE), perfluoroethyl vinyl ether (PFEVE), perfluoropropyl vinyl ether (PFPVE), vinyl fluoride (VF), vinylidene fluoride (VIDF), and perfluoromethoxy vinyl ether (PFMOVE).

In some aspects, the fluorovinyl monomer is selected from a structure having one of the following formulas:
$F_2C=CFR$, where R is H, Cl, a C1-C6 perfluoroalkyl, or OX, where X is a C1-C6 perfluoroalkyl or a C1-C12 perfluorooxyalkyl having one or more ether groups,
or
$H_2C=CR_1R_2$, where $R_1$ is F, H, C1-C6 perfluoroalkyl, or OX, or where X is a C1-C6 perfluoroalkyl or a C1-C12 perfluorooxyalkyl having one or more ether groups, and $R_2$ is F. C1-C6 perfluoroalkyl, or OX, or where X is a C1-C6 perfluoroalkyl or a C1-C12 perfluorooxyalkyl having one or more ether groups.

Depending on the specific properties of the dioxolane monomer that is used, and the comonomer with which it is polymerized, the resulting copolymer may have a glass transition temperature Tg(c) that is higher or lower than the glass transition temperature of a homopolymer, Tg(h), of the dioxolane monomer. For this effect to be of sufficient utility, Tg(c) is normally at least 5° C., preferably 10° C., lower or higher than the Tg(h).

We use the Flory-Fox equation to calculate the Tg(c) based on the Tg(h) of two monomer's homopolymers. The equation is $$\frac{1}{T_g} = \frac{w_1}{T_{g,1}} + \frac{w_2}{T_{g,2}}.$$

where $w_1$ and $w_2$ are weight fractions of components 1 and 2, respectively.

An important advantage of the present invention is that copolymerization of perfluorinated dioxolane monomers with a fluorovinyl monomer as described above can result in higher membrane selectivity for desired gases than can be obtained using prior art membranes.

Due to their advantageous properties, the membranes and processes of the invention are useful for many gas separation applications. Specific examples include, but are not limited to the separation of various non-fluorinated gases, for example, nitrogen, helium., carbon dioxide, and hydrogen from methane. Such separations are important in natural gas processing, for example.

The gas mixture may contain at least two components, designated component A and component B, that are to be separated from each other and optionally another component or components in the stream. The permeating desired gas may be either a valuable gas that is desired to retrieve as an enriched product, or a contaminant that is desired to remove. Thus, either the permeate stream or the residue stream, or both, may be the useful products of the process.

In certain aspects, the invention is a process for separating two components, A and B, of a gas mixture wherein component A is hydrogen and component B is methane. Such a mixture may he found in a steam reforming process. For example, the process of the invention may be used to recover hydrogen from synthesis gas, to remove carbon dioxide from synthesis gas, or to adjust the ratio of hydrogen to carbon monoxide in synthesis gas.

In certain aspects, the invention is a process for separating two components. A and B, of a gas mixture wherein component A is carbon dioxide and component B is methane. This process may be involved in carbon capture and storage or used in the separation of $CO_2$ from natural gas.

In other aspects, the invention is a process for separating two components, A and B, of a gas mixture wherein component A is nitrogen and component B is methane. This process may be involved in removing nitrogen from nitrogen-contaminated natural gas.

In yet another aspect, the invention is a process for separating two components, A and B, of a gas mixture wherein component A is helium and component B is methane. This process may be useful for producing helium through natural gas extraction and subsequent purification.

BRIEF DESCRIPTION OF THE DRAWINGS

None.

DETAILED DESCRIPTION OF THE INVENTION

The term "gas" as used herein means a gas or a vapor.

The term "polymer" as used herein generally includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic and atactic symmetries.

The term "copolymer" as used for simplicity herein refers to all polymers having at least two different monomer units, and thus includes, terpolymers and any other polymers having more than two different monomer units.

The terms "fully-fluorinated" and "perfluorinated" as used herein are interchangeable and refer to a compound where all of the available hydrogen bonded to carbon have been replaced by fluorine.

The term "membrane" as used herein refers to a thin selective layer supported on an integral or discrete support, such as an integral asymmetric membrane or a composite membrane. The membrane generally has a selective layer thickness of less than 10 µm, and more specifically less than 5 µm.

The invention relates to a process for separating two components, A and B, of a gas mixture. The separation is carried out by running a stream of the gas mixture across a membrane that is selective for the desired component to be separated from another component. The desired component to be separated into the permeate may be either Component A or Component B. The process results, therefore, in a permeate stream enriched in the desired component and a residue stream depleted in that component.

At least the selective layer responsible for the gas discriminating properties of the membrane is made from a glassy copolymer. The copolymer should be substantially amorphous. Crystalline polymers are typically essentially insoluble and thus render membrane making difficult, as well as exhibiting generally very low gas permeabilities. Crystalline polymers are not normally suitable for the selective layer, therefore.

The selective layer copolymer should be fluorinated, and generally the degree of fluorination should be high to increase the chemical inertness and resistance of the material. By high, we mean having a fluorine:carbon ratio of atoms in the polymer of at least 1:1. Most preferably, the polymer is perfluorinated, even if the perfluorinated structure has less than a 1:1 fluorine:carbon ratio.

Various copolymeric materials may be used for the copolymeric selective layer to meet the characterizing requirements. These include copolymers comprising a dioxolane monomer and a fluorovinyl monomer.

The dioxolane monomers as described herein are characterized by a 1,3-dioxolane ring, having the general form:

In some embodiments, preferred dioxolane monomers may be selected from perfluoro-2-methylene-1,3-dioxolane derivatives containing various substituent groups at the fourth and fifth positions of the dioxolane ring. These monomers are represented, for example, by the structures found in Monomers A-G of Table 1, above.

A homopolymer of perfluoro-2-methylene-1,3-dioxolane (Monomer H) is crystalline in nature, which was confirmed by Mikeš et al., "Characterization and Properties of Semicrystalline and Amorphous Perfluoropolymer: poly(perfluoro-2-methylene-1,3-dioxolane)," Polymers for Advanced Technologies, v. 22, pp. 1272-1277 (2011), This crystallinity reflects the ability of the repeat unit in the homopolymer of Monomer H to pack tightly, forming ordered structures. As a result, a homopolymer of Monomer H does not dissolve in fluorinated solvents. However, as described herein, copolymerizing a perfluorinated dioxolane monomer with a fluorovinyl monomer, for example, in the appropriate amount may result in an overall amorphous structure, which is desirable for gas separation membrane materials.

Thus, in some embodiments, the fluorovinyl monomer may be selected from the group consisting of trifluoroethylene, tetrafluoroethylene (TFE), chlorotrifluoroethylene (CTFE), perfluoro methyl vinyl ether (PFMVE), perfluoroethyl vinyl ether (PFEVE), perfluoropropyl vinyl ether (PFPVE), vinyl fluoride (VF), vinylidene fluoride (VDF), and perfluoromethoxy vinyl ether (PFMOVE).

Generally, dioxolanes can be prepared by acetalization of aldehydes and ketalization of ketones with ethylene glycol. Formulations embracing those suitable for use in the invention are described in U.S. Pat. Nos. 3,308,107; 5,051,114; 7,754,901; 7,635,780; and 8168,808, incorporated herein by reference. Copolymerization of the amorphous monomers in Table 1 with a fluorovinyl monomer may be carried out in bulk or in solution using 0.1-1.0% of a free radical initiator, such as perfluorodibenzoylperoxide or tert-butyl peroxypivalate. The polymer obtained is purified by precipitating the solution with the addition of a non-solvent, such as dichloromethane. The isolated polymer is dried and the composition is determined by measuring NMR spectrum.

With the fluoropolymers described herein, the bonding of the monomers occurs outside the main dioxolane ring. This process is different than dioxole polymerization, which polymerize by the opening of a double bond within a five-member ring.

In certain embodiments, copolymerization of amorphous perfluorodioxolanes with a fluorovinyl monomer is represented by the following exemplary formula:

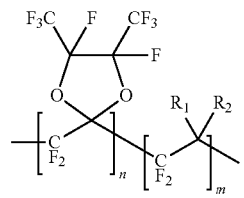

where $R_1$ is F, Cl, H, $OCF_3$, or $OC_3H_7$, and
$R_2$ is F,
and m and n are positive integers.

In certain embodiments, the copolymer may comprise more than one perfluorinated dioxolane monomer or more than one fluorovinyl monomer.

When any pair of monomers is used, one will tend to be more densely packed and perhaps crystalline than the other, and the respective proportions of the two monomers will alter the membrane properties. When copolymerized with the fluorovinyl monomers, the perfluorodioxolanes tend to frustrate polymer chain packing, yielding a selective layer with higher free volume and higher gas permeability. The resulting copolymer is not as crystalline as a fluorovinyl monomer homopolymer and has a higher glass transition temperature. Thus, the copolymer has a glass transition temperature, Tg(c), that is higher, at least 5° C. higher, preferably at least 10° C. higher, than a homopolymer made from the fluorovinyl monomer having a homopolymer glass transition temperature, Tg(h).

Within the range of amorphous copolymers, there is a trade-off between permeance and selectivity. Relatively large proportions of the second monomer decrease permeance in favor of the of selectivity, and relatively large proportions of the first dioxolane monomer decrease selectivity in favor of permeance.

In a preferred embodiment, the copolymer is an ideal random copolymer.

The copolymer chosen for the selective layer can be used to form membranes by any convenient technique known in the art, and may take diverse forms. Because the polymers are glassy and rigid, an unsupported film, tube or fiber of the polymer may be usable in principle as a single-layer membrane. However, such single-layer films will normally be too thick to yield acceptable transmembrane flux, and in practice, the separation membrane usually comprises a very thin selective layer that forms part of a thicker structure. This may be, for example, an integral asymmetric membrane, comprising a dense skin region that forms the selective layer and a microporous support region. Such membranes were originally developed by Loeb and Sourirajan, and their preparation in flat sheet or hollow fiber form is now conventional in the art and is described, for example, in U.S. Pat. Nos. 3,133,132 to Loeb, and U.S. Pat. No. 4,230,463 to Henis and Tripod.

As a further, and a preferred, alternative, the membrane may be a composite membrane, that is, a membrane having multiple layers. Modern composite membranes typically comprise a highly permeable but relatively non-selective support membrane, which provides mechanical strength, coated with a thin selective layer of another material that is primarily responsible for the separation properties. Typically, but not necessarily, such a composite membrane is made by solution-casting the support membrane, then solution-coating the selective layer. General preparation techniques for making composite membranes of this type are well known, and are described, for example, in U.S. Pat. No. 4,243,701 to Riley et al., incorporated herein by reference.

Again, the membrane may take flat-sheet, tube or hollow-fiber form. The most preferred support membranes are those with an asymmetric structure, which provides a smooth, comparatively dense surface on which to coat the selective layer. Support membranes are themselves frequently cast onto a backing, web of paper or fabric. As an alternative to coating onto a support membrane, it is also possible to make a composite membrane by solution-casting the polymer directly onto a non-removable backing web, as mentioned above. In hollow-fiber form, multilayer composite membranes may be made by a coating procedure as taught, for example, in U.S. Pat. Nos. 4,863,761; 5,242,636; and 5,156.888, or by using a double-capillary spinneret of the type taught in U.S. Pat. Nos. 5,141,642 and 5,318,417.

A gutter layer may optionally be used between the support membrane and the selective layer, for example to smooth the support surface and channel fluid to the support membrane pores. In this case, the support membrane is first coated with the gutter layer, then with the perfluoro selective layer as described herein.

Multiple selective layers may also be used.

The thickness of a membrane, as used in the art, normally refers to the thickness of the selective layer or skin of the membrane. The thickness can be chosen according to the proposed use, but will generally be no thicker than 10 μm, or 5 μm, and typically no thicker than 1 μm. It is preferred that the selective layer be sufficiently thin that the membrane provide a pressure-normalized hydrogen flux, as measured with pure hydrogen gas at 25° C., of at least about 100 GPU (where 1 GPU=1×10$^{-6}$ cm$^3$(STP)/cm$^2$-s-cmHg), more preferably at least about 200 GPU and most preferably at least about 400 GPU. In a preferred embodiment, the selective layer thickness is no greater than about 0.5 μm.

Once formed, the membranes exhibit a combination of good mechanical properties, thermal stability, and high chemical resistance. The fluorocarbon polymers that form the selective layer are typically insoluble except in perfluorinated solvents and are resistant to acids, alkalis, oils, low-molecular-weight esters, ethers and ketones, aliphatic and aromatic hydrocarbons, and oxidizing agents, making them suitable for use not only in the presence of $C_{3+}$ hydrocarbons, but in many other hostile environments.

The membranes of the invention may be prepared in any known membrane form and housed in any convenient type of housing and separation unit. We prefer to prepare the membranes in flat-sheet form and to house them in spiral-wound modules. However, flat-sheet membranes may also be mounted in plate-and-frame modules or in any other way. If the membranes are prepared in the form of hollow fibers or tubes, they may be potted in cylindrical housings or otherwise.

The membrane separation unit comprises one or more membrane modules. The number of membrane modules required will vary according to the volume of gas to be treated, the composition of the feed gas, the desired compositions of the permeate and residue streams, the operating pressure of the system, and the available membrane area per module. Systems may contain as few as one membrane module or as many as several hundred or more. The modules may be housed individually in pressure vessels or multiple elements may be mounted together in a sealed housing of appropriate diameter and length.

Of particular importance, the membranes and processes of the invention are useful in applications for producing hydrogen or chemicals from hydrocarbon feedstocks, such as reforming or gasification processes followed by separation or chemical synthesis. Steam reforming is well known in the chemical processing arts, and involves the formation of various gas mixtures commonly known as synthesis gas or syngas from a light hydrocarbon feedstock, steam and optionally other gases, such as air, oxygen or nitrogen. Synthesis gas usually contains at least hydrogen, carbon dioxide, carbon monoxide and methane, but the exact composition can be varied depending on its intended use.

Plant design and process operating conditions thus differ in their details, but the steam reforming process always includes a basic steam/hydrocarbon reforming reaction step, carried out at high temperature and elevated pressure, and one or more subsequent treatments of the raw synthesis gas to remove carbon dioxide or make other adjustments to the gas composition. The processes of the invention are expected to be especially useful in carrying out such treatments.

In another aspect, the invention is a process for separating carbon dioxide from methane, especially if the mixture also contains $C_{3+}$ hydrocarbon vapors. Such a mixture might be encountered during the processing of natural gas, of associated gas from oil wells, or of certain petrochemical streams, for example. The processes of the invention are expected to be useful as part of the gas treatment train, either in the field or at a gas processing plant, for example.

In another aspect, the invention is a process for recovering helium from natural gas. Helium is a rare gas on Earth. Almost all of the commercial helium requirements are supplied by extraction from helium-containing natural gas by low temperature fractional distillation processes. The resulting helium rich gases are further purified or refined using additional cryogenic distillation steps or by pressure swing adsorption (PSA) processes which selectively remove other gases. These final refining steps result in commercial grades of helium in excess of 99.9%. The processes of the invention are expected to be useful in replacing or supplementing one or more of the unit operations in the helium recovery plant.

In yet another aspect, the invention is a process for separating nitrogen from natural gas. The goal will often be to reduce the nitrogen content of the natural gas to no more than about 4% nitrogen, which is an acceptable total inerts value for pipeline gas. In other circumstances, a higher or lower nitrogen target value may be required. Once again, the processes of the invention are expected to be useful in field or plant equipment as stand alone or supplementary units to meet the desired nitrogen concentration target.

Additionally, in another aspect, the invention is a process for separating oxygen from nitrogen. Oxygen is used to enhance the combustion of all fuels, enabling improved burning zone control, and lowering emissions. The present invention is expected to yield enriched oxygen that can be used advantageously in combustion processes, such as kilns, or when using low-grade fuels, where reduction in ballast nitrogen is beneficial. Advantageously, this separation may be also be useful for producing nitrogen, where the separated nitrogen can be used in applications where an inert, stable gas is needed, such as in chemical and petrochemical plants, semiconductor manufacturing, vehicle tires, or fuel systems.

In a further aspect, the invention is a process for separating water from alcohols, such as ethanol, particularly bioethanol produced from natural sources. A major drawback to more economical use of bioethanol as a fuel is the energy used to grow the feedstock, to ferment it, and to separate a dry ethanol product from the fermentation broth. The processes of the invention are expected to be useful in lowering the energy costs associated with ethanol separation (dehydration).

The invention, is now illustrated in further detail by specific examples. These examples are intended to further clarify the invention, and are not intended to limit the scope in any way.

EXAMPLE 1

Membrane Preparation

Composite membranes were prepared using copolymer solutions prepared from the Monomers A-G found in Table 1 and copolymerized using the methods described herein.

Membranes were made using different fluorovinyls and different percentages of fluorovinyl monomers from about 20-55 mol %. The experiments established that copolymers and composite membranes having selective layers incorporating the copolymers can be made from the range of materials in Table 1.

The perfluoro selective layers were coated onto support membranes, either on a small water or by hand coating, and the membranes were finished by oven drying. Samples of each finished composite membrane were then cut into 12.6 $cm^2$ stamps.

EXAMPLE 2

Pure-Gas Testing of the Perfluoro Composite Membranes

A selection of the membranes from Example 1 was subjected to gas permeation tests. The membranes were tested in a permeation test-cell apparatus with pure gases at room temperature and 50 psig feed pressure. The gas fluxes of the membranes were measured, and the permeances and selectivities were calculated.

For comparative purposes, tests were also run with membranes having selective layers made from several formulations of Hyflon® AD, Cytop®, and Teflon® AF.

The results for representative copolymers having different proportions of fluorovinyl monomers are shown in Tables 2-4, below.

TABLE 2

Pure-Gas Selectivity Results

| Sample | Type and Percentage of Fluorovinyl Monomer | Pure-Gas Selectivity | |
| --- | --- | --- | --- |
| | | $H_2/CH_4$ | $CO_2/CH_4$ |
| Polymer 1 | 30 mol % CTFE | 200 | 50 |
| Polymer 2 | 55 mol % CTFE | 90 | 30 |
| Polymer 3 | 53 mol % PFPVE | 10 | 10 |
| Polymer 4 | 53 mol % 3,3,3-trifluoro-2-(trifluoromethyl)-1-propene | 6.0 | 7.0 |
| Polymer 5 | 23 mol % VDF | 80 | 30 |
| Hyflon ® AD60 | | 20 | 20 |
| Hyflon ® AD40 | | 40 | 20 |
| Cytop ® | | 50 | 30 |
| Teflon ® AF2400 | | 5.0 | 6.0 |

EXAMPLE 3

Reproducibility Testing

TABLE 4

Pure-Gas Permeation Results for a Copolymer of 70 mol % D/30 mol % CTFE

| Stamps | Permeance (gpu) | | | Selectivity | | | | |
|---|---|---|---|---|---|---|---|---|
| | $H_2$ | He | $CO_2$ | $N_2/CH_4$ | $O_2/N_2$ | $H_2/CH_4$ | $He/CH_4$ | $CO_2/CH_4$ |
| 1 | 360 | 820 | 90 | 6.0 | 5.0 | 190 | 440 | 50 |
| 2 | 340 | 770 | 80 | 6.0 | 5.0 | 210 | 480 | 50 |
| 3 | 260 | 710 | 60 | 6.0 | | 200 | 540 | 50 |
| 4 | 300 | 760 | 70 | 5.0 | | 160 | 410 | 40 |
| Homopolymer of D | 1,800 | 2,530 | 1,070 | 3.0 | | 34 | 48 | 20 |
| Hyflon ® AD60 | 1,700 | 2,600 | 1,300 | 2.0 | | 20 | 30 | 20 |
| Hyflon ® AD40 | 450 | 1,120 | 270 | 3.0 | | 40 | 90 | 20 |
| Cytop ® | 290 | 790 | 150 | 3.0 | | 50 | 130 | 30 |
| Teflon ® AF2400 | 10,000 | 10,000 | 13,000 | 1.0 | | 5.0 | 5.0 | 6.0 |

Samples 1-4 were tested to check for reproducibility of performance data. The results for Samples 1-4 were also compared to data from a homopolymer of Monomer D.

EXAMPLE 4

Reproducibility Testing

TABLE 5

Pure-Gas Permeation Results for a Copolymer of 45 mol % D/55 mol % CTFE

| Stamps | Permeance (gpu) | | | Selectivity | | | | |
|---|---|---|---|---|---|---|---|---|
| | $H_2$ | He | $CO_2$ | $N_2/CH_4$ | $H_2/CH_4$ | $He/CH_4$ | $CO_2/CH_4$ | |
| 1 | 210 | 520 | 70 | 3.0 | 80 | 200 | 30 | |
| 2 | 230 | 590 | 90 | 3.0 | 60 | 160 | 20 | |
| 3 | 160 | 410 | 50 | 3.0 | 90 | 240 | 30 | |
| Homopolymer of D | 1,800 | 2,530 | 1,070 | 3.0 | 34 | 48 | 20 | |
| Hyflon ® AD60 | 1,700 | 2,600 | 1,300 | 2.0 | 20 | 30 | 20 | |
| Hyflon ® AD40 | 450 | 1,100 | 270 | 3.0 | 40 | 90 | 20 | |
| Cytop ® | 290 | 790 | 150 | 3.0 | 50 | 130 | 30 | |
| Teflon ® AF2400 | 10,000 | 10,000 | 13,000 | 1.0 | 5.0 | 5.0 | 6.0 | |

Samples 1-3 were tested to check for reproducibility of performance data. The results for Samples 1-3 were also compared to data from a homopolymer of Monomer D.

As can be seen from Tables 3-5, in most cases copolymers with CTFE have better selectivity performance for pure gas than Teflon®, Hyflon® or Cytop®.

We claim:

1. A process for separating two components, A and B, of a gas mixture having a ratio (Rf) of A:B, comprising:
   (a) passing the gas mixture across a separation membrane having a feed side and a permeate side, the separation membrane having a selective layer comprising a copolymer consisting of a perfluorinated dioxolane monomer and a fluorovinyl monomer selected from one of the following formulas:

$F_2C=CFR$, where R is H, Cl, a C1-C6 perfluoroalkyl, or OX, where X is a C1-C6 perfluoroalkyl or a C1-C12 perfluorooxyalkyl having one or more ether groups, or $H_2C=CR_1R_2$, where $R_1$ is F, H, C1-C6 perfluoroalkyl, or OX, or where X is a C1-C6 perfluoroalkyl or a C1-C12 perfluorooxyalkyl having one or more ether groups, and $R_2$ is F, C1-C6 perfluoroalkyl, or OX, or where X is a C1-C6 perfluoroalkyl or a C1-C12 perfmorooxyalkyl having one or more ether groups, (b) providing a driving force for transmembrane permeation;
   (c) withdrawing from the permeate side a permeate stream having a ratio (Rp) of A:B, where Rp>Rf; and
   (d) withdrawing from the feed side a residue stream having a ratio (Rr) of A:B, where Rr<Rf.

2. The process of claim 1, wherein the fluorovinyl monomer is selected from the group consisting of trifluoroethylene, chlorotrifluoroethylene (CTFE), perfluoro methyl vinyl ether (PPM VP), perfluoroethyl vinyl ether (PFEVE), perfluoropropyl vinyl ether (PFPVE), vinyl fluoride (VP), vinylidene fluoride (VDF), and perfluoromethoxy vinyl ether (PFMOVE).

3. The process of claim 1, wherein the perfluorinated dioxolane monomer is selected from the group consisting of:

(Monomer A)

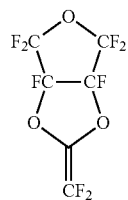

Perfluorotetrahydro-2-
methylene-furo[3,4-d]
[1,3]dioxolane (Monomer B)

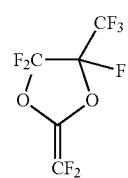

Perfluoro-2-methylene-
4-methyl-1,3,-dioxolane (Monomer C)

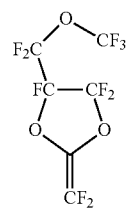

Perfluoro-2-methylene-
4-methoxymethyl-
1,3-dioxane (Monomer D)

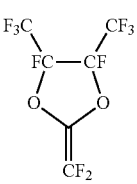

Perfluoro-2-methylene-
4,5-dimethyl-1,3,-dioxolane (Monomer E)

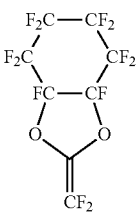

Perfluoro-3-methylene-
2,4-dioxabicyclo
[4,3,0]nonane (Monomer F)

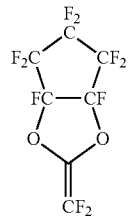

Perfluoro-3-methylene-
2,4-dioxabicyclo-
[3,3,0]octane (Monomer G)

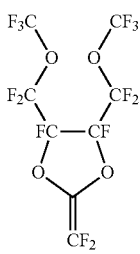

Perfluoro-2-methylene-4,5-
dimethoxymethyl-1,3-dioxolane.

4. The process of claim 1, wherein the gas mixture comprises at least one gas selected from the group consisting of helium, hydrogen, oxygen, nitrogen, methane, and carbon dioxide.

5. The process of claim 1, wherein component A is hydrogen.

6. The process of Claim 1, wherein component A is carbon dioxide.

7. The process of claim 1, wherein component A is nitrogen.

8. The process of claim 1, wherein component A is helium.

9. The process of claim 1, wherein component B is methane.

10. The process of claim 1, wherein the gas mixture further comprises methane and $C_3$ hydrocarbon vapors.

11. The process of claim 1, wherein component A is nitrogen and component B is methane.

12. The process of claim 1, wherein component A is carbon dioxide and component B is methane.

13. The process of claim 1, wherein component A is hydrogen and component B is methane.

14. The process of claim 1, wherein component A is helium and component B is Methane.

15. The process of claim 1, wherein the separation membrane has a selective layer of thickness less than 10 μm.

\* \* \* \* \*